US006430214B1

(12) United States Patent
Jalloul et al.

(10) Patent No.: US 6,430,214 B1
(45) Date of Patent: Aug. 6, 2002

(54) FADING RESISTANT MULTI-LEVEL QAM RECEIVER

(75) Inventors: Louay Jalloul, Palatine; Amitava Ghosh, Vernon Hills, both of IL (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/576,367

(22) Filed: May 22, 2000

(51) Int. Cl.[7] .......................... H04L 27/30; H04L 5/12; H04L 23/02
(52) U.S. Cl. ........................ 375/147; 375/130; 375/261
(58) Field of Search ................................. 375/147, 210, 375/200, 130, 261; 370/320

(56) References Cited

U.S. PATENT DOCUMENTS

| | | | | |
|---|---|---|---|---|
| 5,218,619 A | * | 6/1993 | Dent | 375/209 |
| 5,305,349 A | * | 4/1994 | Dent | 375/209 |
| 5,608,722 A | * | 3/1997 | Miller | 370/320 |
| 5,724,378 A | * | 3/1998 | Miki et al. | 375/200 |
| 5,734,647 A | * | 3/1998 | Yoshida et al. | 370/335 |
| 5,768,307 A | * | 6/1998 | Schramm et al. | 375/208 |
| 5,930,230 A | * | 7/1999 | Odenwalder et al. | 370/208 |
| 5,943,361 A | * | 8/1999 | Gilhousen et al. | 375/200 |
| 6,115,427 A | * | 9/2000 | Calderbank et al. | 375/267 |
| 6,192,068 B1 | * | 2/2001 | Fattouche et al. | 375/200 |

OTHER PUBLICATIONS

Effect of Channel Estimation Error on M–QAM BER Performance in Rayleigh Fading, Xiaoyi Tang, Mohamed–Slim Alouini, Member, IEEE, and Andrea J. Goldsmith, Senior Member, IEEE, Transactions on Communications, vol. 47, No. 12, 12/99 pp. 1856–1864.

Rayleigh Fading Compensation for QAM in Land Mobile Radio Communications, Seiichi Sampei and Terumi Sunage, Transactions on Vehicular Technoclogy, vol. 42, No. 2, May 1993 pp. 137–147.

Principles of Spread spectrum Communication, Andrew J. Viterbi, Addison–Wesley Publishing Co., Chapter 4 pp. 77–105.

An Intuitive Justification and a Simplified Implementation of the MAP Decoder for Convolutional Codes, Andrew J. Viterbi, Life Fellow, IEEE, IEEE Journal on Selected Areas in Communications, vol. 16, No. 2 2/98 pp. 260–264.

Near Shannon Limit Error–Correcting Coding and Decoding: Turbo–Codes (1), Claude Berrou, Alain Glavieus & Punya Thitimajshima, pp. 1064–1070.

* cited by examiner

*Primary Examiner*—Chi Pham
*Assistant Examiner*—Tony Al-Beshrawi
(74) *Attorney, Agent, or Firm*—Scott M. Garrett

(57) ABSTRACT

An architecture for simplified automatic gain control circuit (100, 200, 300) that is useable with M-ary QAM systems to improve overall link performance. The implementations particularly relating to modulating an M-ary QAM constellation according to a set of estimates derived from the pilot channel(s) and/or the traffic channels, modulating the M-ary QAM constellation according to the values of the pilot and traffic channel gains that are being sent to a mobile wireless device on a control channel, and using a power control bit at the mobile wireless device to modulate the M-ary QAM constellation, all resulting in improved receiver performance.

13 Claims, 3 Drawing Sheets

FADING RESISTANT MULTI-LEVEL QAM RECEIVER

FIELD OF THE INVENTION

This invention relates in general to quadrature amplitude modulation (QAM) receivers and more particularly to a fading resistant quadrature amplitude modulation receiver.

BACKGROUND OF THE INVENTION

In products such as a wireless device or the like, many different schemes exist to convey information from a transmitter to its receiver. Conventional voice communication systems such as the IS-95 based CDMA system use digital modulation schemes such as Binary Phase Shift Keying (BPSK) or Quadrature Phase Shift Keying (QPSK) to convey voice information to the wireless device. Market conditions and advances in technology have pressed designers of wireless devices to use more exotic information delivery schemes such as multi-level QAM in an attempt to increase the information carrying capacity or spectral efficiency of a wireless communication system. These changes, however, and not without their problems. Higher order modulation schemes such as 8 PSK or 16, 32 and 64 QAM are particularly susceptible to conditions such as Rayleigh fading, a phenomena that creates widely varying signal strength conditions at the receiver. As such the Eb/NO requirement at the receiver to decode a multi-level QAM signal is much higher than the Eb/No requirement to decode a BPSK/QPSK signal.

Thus, what is needed is a system and method for the detection and correction of fading signal conditions in a QAM receiver, resulting in improved information signal recovery.

DESCRIPTION OF A PREFERRED EMBODIMENT

Higher order modulation is a technique for increasing the channel spectral efficiency. Both 16 and 64-QAM are proposed for use in state of the art communication systems, as well as 8-PSK and 16-QAM which are used in the high data rate (HDR) CDMA systems. Since real radio channels exist in a Rayleigh fading environment, an intelligent compensation circuit is needed to enable a receiver to effectively demodulate a desired QAM constellation. This is not a trivial matter since higher order QAM constellations, although symmetric in design, are effected by signal multipath conditions, resulting in a highly asymmetric constellation which needs to be corrected in order for the information to be properly recovered.

Prior art fading compensation methods require the receiver to divide the received symbol by the magnitude of the fading channel envelope, if it can be determined. This method is inaccurate at best, since the detected envelope is influenced by both long and short term signal characteristics. The result is a correction based on a best guess of the average signal power of the detected envelope. A small error in the magnitude of the fading amplitude would result in a large enhancement of the noise and interference terms in the demodulated symbol that is input to the decoder. Moreover, the process of division, although easily performed in a numerical simulation, is neither practical or possible in a real implementation that would be implemented in a mass produced wireless information product. Further in systems employing higher order QAM modulation, the Pilot Gain to Traffic Channel Gain ratio was fixed (example GSM EDGE systems). However, in the state of art CDMA forward link, the Pilot Gain to Traffic Channel Gain ratio can vary on a frame by frame basis which makes the recovery of QAM signals difficult in practice.

In this invention, three new practical architectures for fading compensation of M-ary QAM signals are shown for a CDMA system where the Pilot Gain to Traffic Channel Gain ratio varies on a frame by frame basis. The receiver structures shown are both practical and realizable. Furthermore, the architectures yield significant improvements in demodulation and decoding performance in both high and marginal signal power regions.

Figure 1:
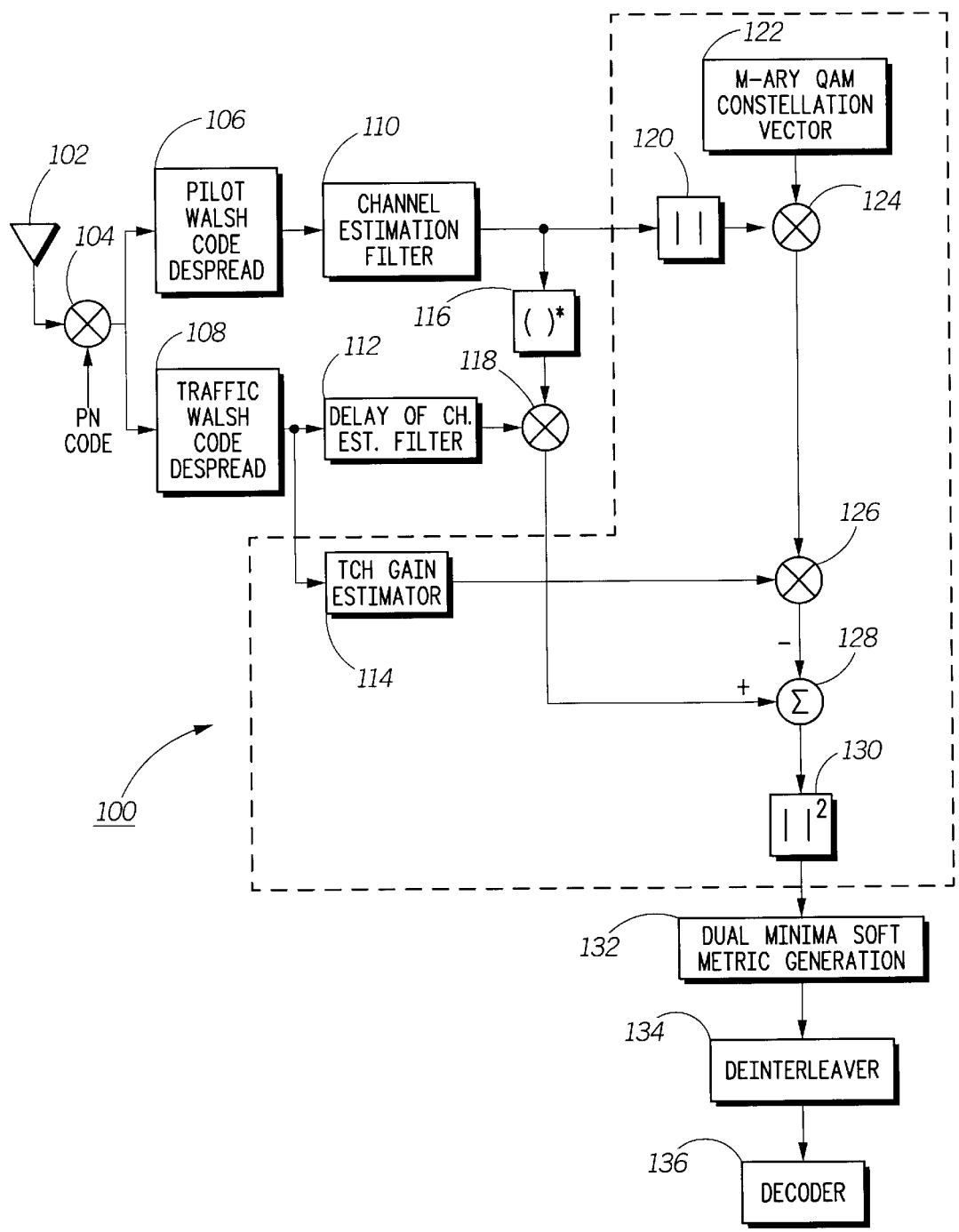
FIG. 1 is a block diagram of a wireless device with a M-ary QAM demodulator in accordance with a first embodiment of the present invention.
Figure 3:
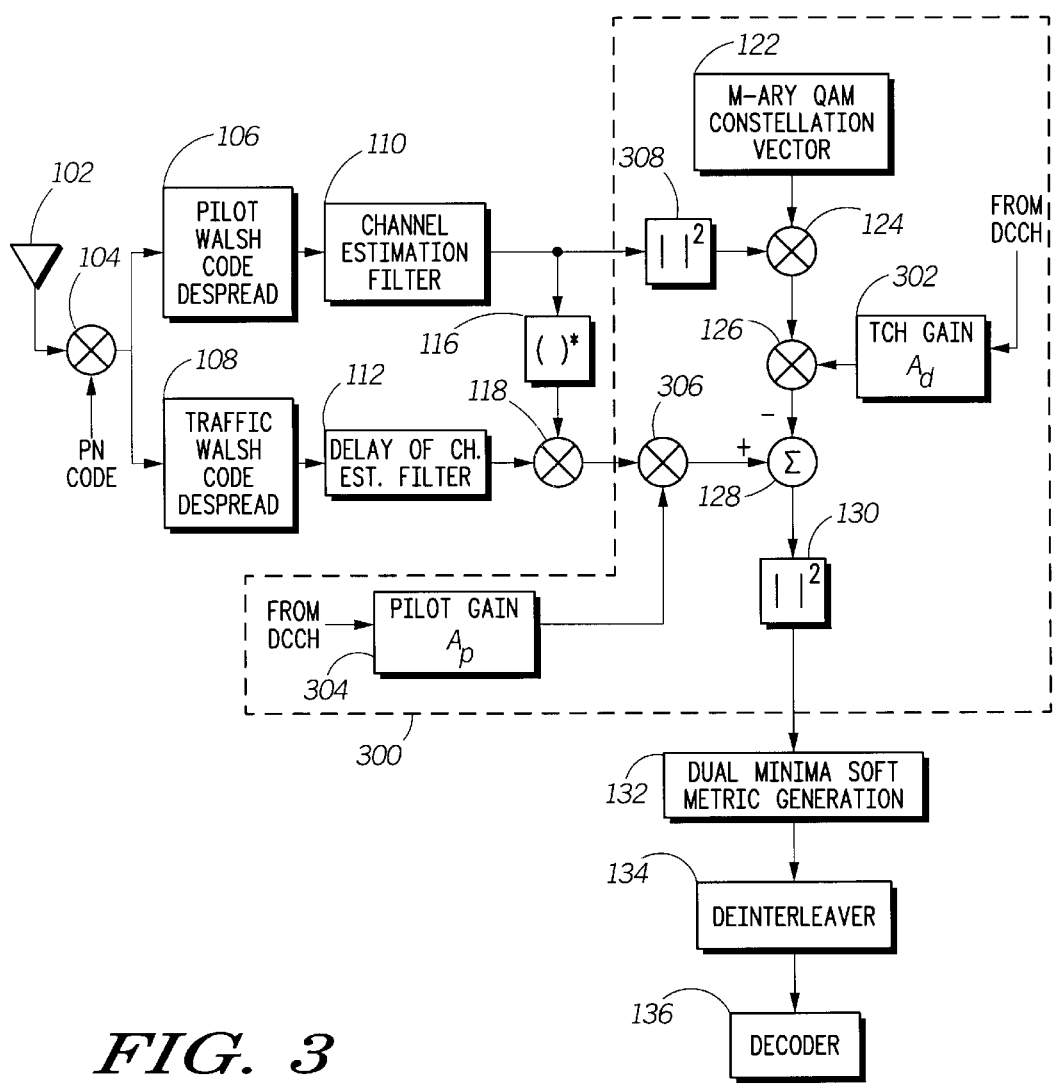
FIG. 3 is a block diagram of a wireless device with a M-ary QAM demodulator in accordance with a second embodiment of the present invention.
Figure 4:
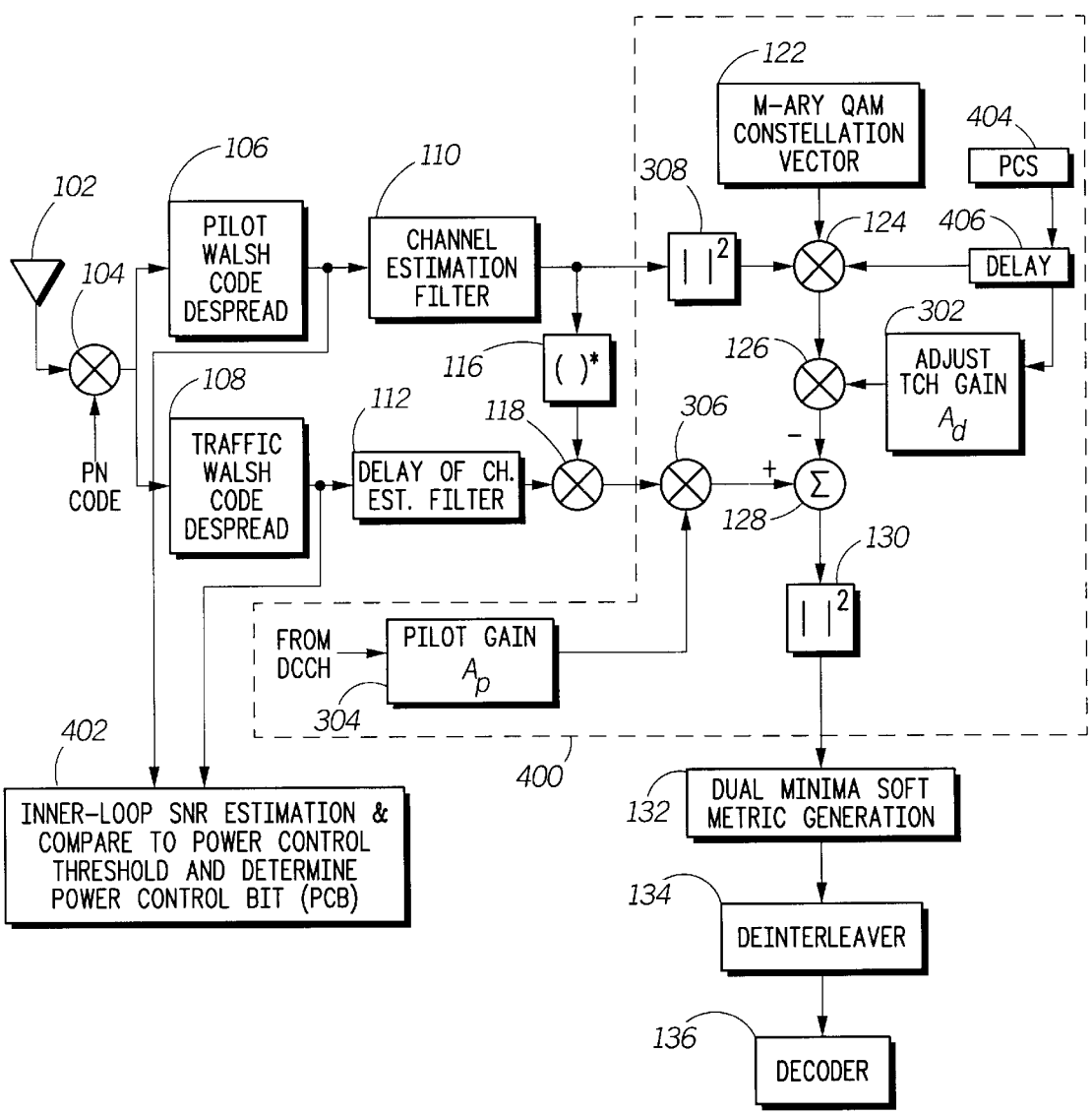
FIG. 4 is a block diagram of a wireless device with a M-ary QAM demodulator in accordance with a third embodiment of the present invention.

The M-ary QAM demodulator illustrated in FIGS. 1, 3 and 4 generates soft decisions as inputs to a conventional Turbo decoder. The soft inputs are generated by an approximation to the log likelihood ratio function as follows. First we define, $$\Lambda^{(i)}(z) = K_f \left[ \min_{j \in S_i} \{d_j^2\} - \min_{j \in \bar{S}_i} \{d_j^2\} \right], \quad i = 0, 1, 2, \ldots, \log_2 M - 1 \quad [1]$$

where M is the modulation alphabet size, e.g., 8, 16, 32 or 64, and $$z = A_d A_p \alpha \hat{\alpha} e^{-j(\theta + \hat{\theta})} x + n, \quad [2]$$

where x is the transmitted QAM symbol, $A_d$ is the traffic channel gain, $A_p$ is the pilot channel gain, $\alpha e^{j\theta}$ is the fading channel gain, and $A_p \hat{\alpha} e^{j\hat{\theta}}$ the fading channel estimate obtained from the pilot channel. Furthermore, $$S_i = \{\forall j : i^{th} \text{ component of } y_j \text{ is "0"}\}, \quad [3]$$

$$\bar{S}_i = \{\forall j : i^{th} \text{ component of } y_j \text{ is "1"}\} \quad [4]$$

and $K_f$ is a scale factor proportional to the received signal-to-noise ratio. The parameter $d_j$ is the Euclidean distance of the received symbol z from the points on the QAM constellation. This distance metric will be used in the following discussion of the three unique architectures for effectively recovering, demodulating, and decoding the information intended for delivery to the wireless device.

Referring to FIG. 1, a first receiver architecture is illustrated that is adapted for dealing with the case of unknown pilot and traffic channel gains.

In this case, the receiver is unaware of the fraction of the total power allocated to the pilot channel, nor is it aware of the traffic channel fraction of allocated power. In this case, the distance metric is computed as follows:

$$d_j^2 = |z - Q_j \beta \gamma|^2 \quad [5]$$

where $Q_j$ are the points on the M-ary QAM constellation and $\beta = A_d \hat{\alpha}$ is an estimate formed from the traffic channel despread data, and $\gamma = A_p \hat{\alpha}$ is an estimate formed from the pilot channel after processing through the channel estimation filter 110 as shown in FIG. 1.

The fading resistant multi-level QAM receiver shown in FIG. 1 comprises an antenna 102 for receiving a code division multiple access spread spectrum information signal comprising a traffic channel and a pilot channel. A first mixer 104 is coupled to the antenna, the first mixer operating to multiply the code division multiple access spread spectrum information signal by an appropriate pseudo-random numerical code sequence (PN code) to generate a converted code division multiple access spread spectrum information signal. A pilot channel Walsh code despreader 106 is coupled to the first mixer 104. The pilot channel Walsh code despreader operates to despread the converted code division multiple access spread spectrum information signal. A channel estimation filter 110 is coupled to the pilot Walsh code despreader 106, the channel estimation filter 110 operating to determine an estimate of an amplitude and phase associated with the pilot channel. A conjugate generator 116 is coupled to the channel estimation filter 110. The conjugate generator 116 operates to determine a complex conjugate of the estimate of the amplitude and phase associated with the pilot channel.

Now considering the traffic channel signal path, a traffic channel Walsh code despreader 108 is coupled to the first mixer 104, the traffic channel Walsh code despreader 108 operating to despread the converted code division multiple access spread spectrum information signal. A delay of channel estimation filter 112 is coupled to the traffic channel Walsh code despreader 108, the delay of channel estimation filter 112 operating to determine an estimate of a delay necessary for proper time alignment of the pilot channel and the traffic channel for demodulation. This is necessary since improper time alignment will result in imperfect or possibly no decoding of a demodulated signal. A second mixer 118 is coupled to the conjugate generator 116 and to the delay of channel estimation filter 112, the second mixer 118 operating to multiply the complex conjugate of the estimate of the phase and amplitude associated with the pilot channel by a delayed representation of the traffic channel.

The fading compensation circuitry is shown within the outline 100, and comprises the following elements. A magnitude generator 120 is coupled to the channel estimation filter 110, the magnitude generator operating to determine an estimated amplitude associated with the pilot channel. A third mixer 124 is coupled to the magnitude generator and an M-ary QAM constellation generator 122 that operates to generate an M-ary QAM constellation vector reference. The third mixer operates to multiply the estimated power associated with the pilot channel by the M-ary QAM constellation vector reference, creating a scaled (in proportion to the estimated power associated with the pilot channel) version of the M-ary QAM constellation vector reference. A traffic channel gain estimator 114 is coupled to the traffic channel Walsh code despreader 108, the traffic channel gain estimator 114 operating to determine an estimated amplitude associated with the traffic channel. A fourth mixer 126 coupled to the third mixer 124 and to the traffic channel gain estimator 114, operates to multiply a result of the third mixer (discussed above) by the estimated amplitude associated with the traffic channel.

A summer 128 is coupled to the second mixer 118 and to the fourth mixer 126. The summer 128 operates to subtract a result of the fourth mixer 126 from a result of the second mixer 118. Consequently, a magnitude squared generator 130 is coupled to the summer 128, the magnitude squared generator operating to determine a Euclidean distance metric associated with each M-ary QAM modulation point. At this point the received signal has been corrected with respect to any amplitude variations that may have distorted a received point in the M-ary QAM constellation. The corrected signal is then coupled from the magnitude squared generator 130 to a dual minima soft metric generator 132 that operates to generate a soft decision for each bit comprising a channel symbol. A de-interleaver 134 is coupled to the dual minima soft metric generator 132, the de-interleaver 134 operating to deinterleave the channel symbols. Finally, a decoder 136 is coupled to the de-interleaver 134, the decoder 136 operating to decode the channel symbols into information bits representing a transmitted message.

Figure 2:
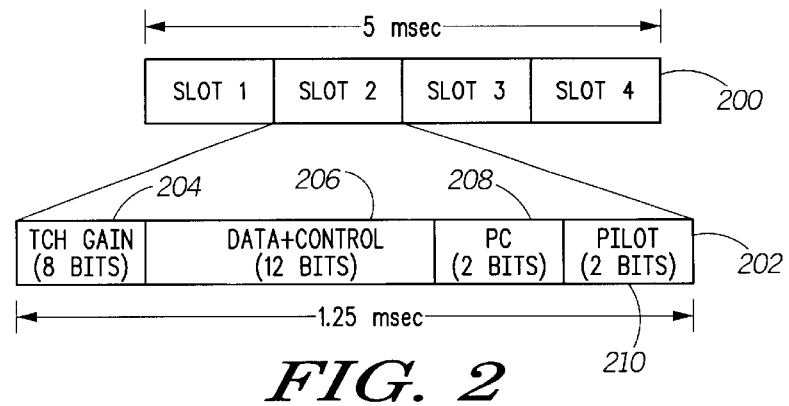
FIG. 2 is a protocol diagram of a control channel for use with the wireless device.

Referring to FIG. 2, the protocol diagram shows and exemplary control channel for use with the wireless device.

Preferably, each control segment 202 in the control channel 200 comprises slots that are assigned to one or more receivers. Each slot comprises a transmit channel gain parameter (TCH gain, 8 bits) 204, data and control information 206 (12 bits), power control information 208 (2 bits) and pilot channel information 210 (2 bits). The use of this information will be explained in conjunction with the second and third embodiments of the present invention. Furthermore, one of ordinary skill in the art would realize that the selection of 2, 8, 12, or any other reasonable number of bits, for the preceding parameters, is a matter of design choice, and may be freely varied without deviating from the spirit of the present invention.

Referring to FIG. 3, the block diagram illustrates an architecture that can make use of information shown in the control channel 200 to effect proper correction of received M-ary QAM information. In this case, a base station would transmit the mobile gain of the traffic channel on the dedicated control channel 200 (DCCH). The traffic channel gain $A_d$ is preferably an eight bit number (e.g., the maximum gain would be limited to 127 in this example). The pilot gain would be transmitted on a synchronization channel at the initiation of a communication session. In this case, the distance metric is computed as follows:

$$d_j^2 = |A_p z - Q_j \beta \gamma^*|^2 \qquad [6]$$

where $\beta = A_d$ and $\gamma = A_p \hat{\alpha}$ is an estimate formed from the pilot channel after processing through the channel estimation filter as shown in FIG. 3.

Since the antenna 102, first mixer 104, pilot channel Walsh code despreader 106, channel estimation filter 110, conjugate generator 116, traffic channel Walsh code despreader 108, delay of channel estimation filter 112, and second mixer 118 are identical in structure and operation to that discussed with reference to FIG. 1, the prior discussion of these elements is incorporated herein by reference thereto.

The fading compensation circuitry is shown within the outline 300, and comprises a first magnitude squared generator 308, is coupled to the channel estimation filter 112. The magnitude squared generator 308 operates to determine an estimated power associated with the pilot channel. The third mixer 124 is coupled to the magnitude squared generator 308 and the M-ary QAM constellation generator 122. The third mixer 124 operates to multiply the magnitude of the estimated power associated with the pilot channel by the M-ary QAM constellation vector reference. A sixth mixer 126 is coupled to the third mixer 124 and has an input signal representing a traffic channel gain determined from a traffic channel power gain parameter 204 broadcast to the fading resistant multi-level QAM receiver. The sixth mixer 126 operates to multiply a result of the third mixer 124 by the traffic channel gain. A seventh mixer 306 is coupled to the second mixer 118 and has an input signal representing a pilot channel gain determined from a pilot channel power gain parameter broadcast to the fading resistant multi-level QAM receiver. The seventh mixer 306 operates to multiply a result of the second mixer 118 by the input signal representing the pilot channel gain. A summer 128 is coupled to the sixth mixer 126 and to the seventh mixer 306, the summer 128 operating to subtract a result of the sixth mixer 126 from a result of the seventh mixer 306. A second magnitude squared generator 130 is coupled to the summer 128, the second magnitude squared generator operating to determine a Euclidean distance metric associated with each M-ary QAM modulation point. Just as with the architecture shown in FIG. 1, the correction is complete as this point in the signal flow. However, in the case of the architecture shown in FIG. 3, the correction metric uses equation [6] for correction, and should perform better based on the fact that that ratio of the control channel to the traffic channel power is known absolutely from channel data, rather than estimated from recovered channel modulation or the like. As one of ordinary skill in the art should appreciate, the preceding architectures may be combined in situations where a system doesn't support channel gain value transmissions, yielding still another improvement over prior art systems.

As with the architecture shown in FIG. 1, the corrected signal is then coupled from the magnitude squared generator 130 to a dual minima soft metric generator 132 that operates to generate a soft decision for each bit comprising a channel symbol. A de-interleaver 134 is coupled to the dual minima soft metric generator 132, the de-interleaver 134 operating to deinterleave the channel symbols. Finally, a decoder 136 is coupled to the de-interleaver 134, the decoder 136 operating to decode the channel symbols into information bits representing a transmitted message.

Referring to FIG. 4, the block diagram illustrates an architecture that can make use of information shown in the control channel 200 in conjunction with as information derived from actual channel statistics, to effect proper correction of received M-ary QAM information.

In this case the traffic channel gain is initialized to a predetermined fixed value known to the receiver. Based on a power control bit (PCB) that is determined from the inner-loop power control measurement of the received signal to noise ratio (SNR) and comparison to a power control threshold (e.g., such as an 800 Hz update rate forward power control), a gain value is updated at the receiver. As long as the PCB is not received at a base station receiver in error, the gain at the mobile receiver and the base station transmitter will be the same. Thus, any error on a reverse link is controlled to a low value using the architecture illustrated in FIG. 4.

Since the antenna 102, first mixer 104, pilot channel Walsh code despreader 106, channel estimation filter 110, conjugate generator 116, traffic channel Walsh code despreader 108, delay of channel estimation filter 112, and second mixer 118 are identical in structure and operation to that discussed with reference to FIGS. 1 and 3, the prior discussion of these elements is incorporated herein by reference thereto.

Beginning at a signal to noise ratio estimator 402, it is coupled to at least one of the pilot channel Walsh code despreader 106 and the traffic channel Walsh code despreader 108, the signal to noise ratio estimator 402 operating to determine an estimated signal to noise ratio associated with at least the traffic channel, and further generating a power control signal when the estimated signal to noise ratio associated with at least the traffic signal is other than a predetermined signal to noise ratio necessary for optimal demodulation of information associated with the traffic channel. Thus, a maximum or minimum SNR threshold may be chosen, above or below which the signal to noise ratio estimator 402 will generate the power control signal, representing whether the power needs to be adjusted up or down. Conversely, the maximum and minimum may be exchanged and the adjustments would switch in a corresponding manner, resulting in adjustments down or up. The order of this arrangement is one of design choice typically dictated by hardware constraints in realizing the actual physical implementation.

The fading compensation circuitry is shown within the outline 400, and comprises a first magnitude squared generator 308 is coupled to the channel estimation filter 112, the magnitude squared generator 308 operating to determine an estimated power associated with the pilot channel. A third mixer 124 is coupled to the magnitude squared generator 308 and an M-ary QAM constellation generator 122 that operates to generate an M-ary QAM constellation vector reference. The third mixer 124 operates to multiply the estimated power associated with the pilot channel by the M-ary QAM constellation vector reference, as was discussed with reference to FIG. 3.

In this embodiment, a delay generator 406 responsive to the power control signal 404, is coupled to the third mixer 124. The delay generator 406 operates to select a predetermined time delay after which a traffic channel gain is adjusted according to the power control signal 404. This operation allows proper, accurate adjustment of the traffic channel gain, resulting in improved receiver demodulation performance.

A sixth mixer 126 is coupled to the third mixer 124 and to the delay generator 406 that provides an input signal representing the traffic channel gain. The sixth mixer 126 operates to multiply a result of the third mixer 124 by the traffic channel gain. A seventh mixer 306 is coupled to the second mixer 118 and has an input signal representing the pilot channel gain determined from the pilot channel power gain parameter broadcast to the fading resistant multi-level QAM receiver. The seventh mixer 306 operates to multiply a result of the second mixer 118 by the input signal representing the pilot channel gain 304. A summer 128 is coupled to the sixth mixer 126 and to the seventh 306 mixer, the summer 128 operating to subtract a result of the sixth mixer 126 from a result of the seventh mixer 306.

A second magnitude squared generator 130 is coupled to the summer 128, the second magnitude squared generator operating to determine a Euclidean distance metric associated with each M-ary QAM modulation point. Just as with the architecture shown in FIGS. 1 and 3, the correction is complete as this point in the signal flow. However, in the case of the architecture shown in FIG. 4, the correction metric not only uses equation [6] for correction (and may also use the like elements from FIG. 3), but it further predictively corrects the traffic channel gain. As one of ordinary skill in the art should appreciate, any of the preceding architectures may be combined in situations where a system either doesn't support channel gain value transmissions, or has poor reverse channel power reaction characteristics (at a base station), yielding still further improvements over prior art systems.

As with the architecture shown in FIGS. 1 and 3, the corrected signal is then coupled from the magnitude squared generator 130 to a dual minima soft metric generator 132 that operates to generate a soft decision for each bit comprising a channel symbol. A de-interleaver 134 is coupled to the dual minima soft metric generator 132, the de-interleaver 134 operating to deinterleave the channel symbols. Finally, a decoder 136 is coupled to the de-interleaver 134, the decoder 136 operating to decode the channel symbols into information bits representing a transmitted message.

In summary, the architectures disclosed herein lend themselves to practical hardware implementations. The final results are simplified automatic gain control circuits that are useable with M-ary QAM systems to improve overall link performance. This invention particularly uses techniques relating to (1) modulating the M-ary QAM constellation according to a set of estimates derived from the pilot channel(s) and/or the traffic channels, (2) modulating the M-ary QAM constellation according to the values of the pilot and traffic channel gains that are being sent to a mobile wireless device on a control channel, and (3) using a power control bit at the mobile wireless device to modulate the M-ary QAM constellation, all resulting in improved receiver performance.

We claim:

1. A fading resistant multi-level QAM receiver, comprising:

an antenna;

a first mixer coupled to the antenna and to a pilot channel Walsh code despreader and a traffic channel Walsh code despreader;

a channel estimation filter coupled to the pilot channel Walsh code despreader and to a conjugate generator;

a delay of channel estimation filter coupled to the traffic channel Walsh code despreader;

a second mixer coupled to the conjugate generator and to the delay of channel estimation filter;

a magnitude generator coupled to the channel estimation filter;

a third mixer coupled to the magnitude generator and an M-ary QAM constellation generator;

a fourth mixer coupled to the third mixer and to a traffic channel gain estimator;

a summer coupled to the second mixer and to the fourth mixer;

a magnitude squared generator coupled to the summer;

a dual minima soft metric generator coupled to the magnitude squared generator;

a de-interleaver coupled to the dual minima soft metric generator; and a decoder coupled to the de-interleaver.

2. A fading resistant multi-level QAM receiver, comprising:

an antenna;

a first mixer coupled to the antenna and to a pilot channel Walsh code despreader and a traffic channel Walsh code despreader;

a channel estimation filter coupled to the pilot channel Walsh code despreader and to a conjugate generator;

a delay of channel estimation filter coupled to the traffic channel Walsh code despreader;

a second mixer coupled to the conjugate generator and to the delay of channel estimation filter;

a magnitude squared generator coupled to the channel estimation filter;

a third mixer coupled to the magnitude squared generator and an M-ary QAM constellation generator;

a fourth mixer coupled to the third mixer and having an input signal representing a traffic channel gain;

a fifth mixer coupled to the second mixer and having an input signal representing a pilot channel gain;

a summer coupled to the fourth mixer and to the fifth mixer;

a second magnitude squared generator coupled to the summer;

a dual minima soft metric generator coupled to the second magnitude squared generator;

a de-interleaver coupled to the dual minima soft metric generator; and a decoder coupled to the de-interleaver.

3. A fading resistant multi-level QAM receiver, comprising:

an antenna;

a first mixer coupled to the antenna and to a pilot channel Walsh code despreader and a traffic channel Walsh code despreader;

a channel estimation filter coupled to the pilot channel Walsh code despreader and to a conjugate generator;

a delay of channel estimation filter coupled to the traffic channel Walsh code despreader;

a second mixer coupled to the conjugate generator and to the delay of channel estimation filter;

a signal to noise ratio estimator coupled to at least one of the pilot channel Walsh code despreader and the traffic channel Walsh code despreader;

a third mixer coupled to a magnitude squared generator and an M-ary QAM constellation generator;

a delay generator responsive to the power control signal and coupled to the third mixer;

a fourth mixer coupled to the third mixer and to the delay generator;

a fifth mixer coupled to the second mixer and having an input signal representing a pilot channel gain determined from a pilot channel power gain parameter broadcast to the fading resistant multi-level QAM receiver;

a summer coupled to the fourth mixer and to the fifth mixer;

a second magnitude squared generator coupled to the summer;

a dual minima soft metric generator coupled to the second magnitude squared generator;

a de-interleaver coupled to the dual minima soft metric generator; and a decoder coupled to the de-interleaver.

4. A fading resistant multi-level QAM receiver, comprising:

an antenna for receiving a code division multiple access spread spectrum information signal comprising a traffic channel and a pilot channel;

a first mixer coupled to the antenna, the first mixer operating to multiply the code division multiple access spread spectrum information signal by an appropriate pseudo-random numerical code sequence to generate a converted code division multiple access spread spectrum information signal;

a pilot channel Walsh code despreader coupled to the first mixer, the pilot channel Walsh code despreader operating to despread the converted code division multiple access spread spectrum information signal;

a channel estimation filter coupled to the pilot Walsh code despreader, the channel estimation filter operating to determine an estimate of an amplitude and phase associated with the pilot channel;

a conjugate generator coupled to the channel estimation filter, the conjugate generator operating to determine a complex conjugate of the estimate of the amplitude and phase associated with the pilot channel;

a traffic channel Walsh code despreader coupled to the first mixer, the traffic channel Walsh code despreader operating to despread the converted code division multiple access spread spectrum information signal;

a delay of channel estimation filter coupled to the traffic channel Walsh code despreader, the delay of channel estimation filter operating to determine an estimate of a delay necessary for proper time alignment of the pilot channel and the traffic channel for demodulation;

a second mixer coupled to the conjugate generator and to the delay of channel estimation filter, the second mixer operating to multiply the complex conjugate of the estimate of the phase and amplitude associated with the pilot channel by a delayed representation of the traffic channel;

a magnitude generator coupled to the channel estimation filter, the magnitude generator operating to determine an estimated amplitude associated with the pilot channel;

a third mixer coupled to the magnitude generator and an M-ary QAM constellation generator that operates to generate an M-ary QAM constellation vector reference, the third mixer operating to multiply the estimated power associated with the pilot channel by the M-ary QAM constellation vector reference;

a traffic channel gain estimator coupled to the traffic channel Walsh code despreader, the traffic channel gain estimator operating to determine an estimated amplitude associated with the traffic channel;

a fourth mixer coupled to the third mixer and to the traffic channel gain estimator, the fourth mixer operating to multiply a result of the third mixer by the estimated amplitude associated with the traffic channel;

a summer coupled to the second mixer and to the fourth mixer, the summer operating to subtract a result of the fourth mixer from a result of the second mixer;

a magnitude squared generator coupled to the summer, the magnitude squared generator operating to determine a Euclidean distance metric associated with each M-ary QAM modulation point;

a dual minima soft metric generator coupled to the magnitude squared generator, the dual minima soft metric generator operating to generate a soft decision for each bit comprising a channel symbol;

a de-interleaver coupled to the dual minima soft metric generator, the de-interleaver operating to deinterleave the channel symbols; and a decoder coupled to the de-interleaver, the decoder operating to decode the channel symbols into information bits representing a transmitted message.

5. A fading resistant multi-level QAM receiver, comprising:

an antenna for receiving a code division multiple access spread spectrum information signal comprising a traffic channel and a pilot channel;

a first mixer coupled to the antenna, the first mixer operating to multiply the code division multiple access spread spectrum information signal by an appropriate pseudo-random numerical code sequence to generate a converted code division multiple access spread spectrum information signal;

a pilot channel Walsh code despreader coupled to the first mixer, the pilot channel Walsh code despreader operating to despread the converted code division multiple access spread spectrum information signal;

a channel estimation filter coupled to the pilot Walsh code despreader, the channel estimation filter operating to determine an estimate of an amplitude and phase associated with the pilot channel;

a conjugate generator coupled to the channel estimation filter, the conjugate generator operating to determine a complex conjugate of the estimate of the amplitude and phase associated with the pilot channel;

a traffic channel Walsh code despreader coupled to the first mixer, the traffic channel Walsh code despreader operating to despread the converted code division multiple access spread spectrum information signal;

a delay of channel estimation filter coupled to the traffic channel Walsh code despreader, the delay of channel estimation filter operating to determine an estimate of a delay necessary for proper time alignment of the pilot channel and the traffic channel for demodulation;

a second mixer coupled to the conjugate generator and to the delay of channel estimation filter, the second mixer operating to multiply the complex conjugate of the estimate of the phase and amplitude associated with the pilot channel by a delayed representation of the traffic channel;

a first magnitude squared generator coupled to the channel estimation filter, the magnitude squared generator operating to determine an estimated power associated with the pilot channel;

a third mixer coupled to the magnitude squared generator and the M-ary QAM constellation generator that generates an M-ary QAM constellation vector reference, the third mixer operating to multiply the magnitude of the estimated power associated with the pilot channel by the M-ary QAM constellation vector reference;

a fourth mixer coupled to the third mixer and having an input signal representing a traffic channel gain determined from a traffic channel power gain parameter broadcast to the fading resistant multi-level QAM receiver, the fourth mixer operating to multiply a result of the third mixer by the traffic channel-gain;

a fifth mixer coupled to the second mixer and having an input signal representing a pilot channel gain determined from a pilot channel power gain parameter broadcast to the fading resistant multi-level QAM receiver, the fifth mixer operating to multiply a result of the second mixer by the input signal representing a pilot channel gain;

a summer coupled to the fourth mixer and to the fifth mixer, the summer operating to subtract a result of the fourth mixer from a result of the fifth mixer;

a second magnitude squared generator coupled to the summer, the second magnitude squared generator operating to determine a Euclidean distance metric associated with each M-ary QAM modulation point;

a dual minima soft metric generator coupled to the second magnitude squared generator, the dual minima soft metric generator operating to generate a soft decision for each bit comprising a channel symbol;

a de-interleaver coupled to the dual minima soft metric generator, the de-interleaver operating to deinterleave the channel symbols; and a decoder coupled to the de-interleaver, the decoder operating to decode the channel symbols into information bits representing a transmitted message.

6. A fading resistant multi-level QAM receiver comprising:

an antenna for receiving a code division multiple access spread spectrum information signal comprising a traffic channel and a pilot channel;

a first mixer coupled to the antenna, the first mixer operating to multiply the code division multiple access spread spectrum information signal by an appropriate pseudo-random numerical code sequence to generate a converted code division multiple access spread spectrum information signal;

a pilot channel Walsh code despreader coupled to the first mixer, the pilot channel Walsh code despreader operating to despread the converted code division multiple access spread spectrum information signal;

a channel estimation filter coupled to the pilot Walsh code despreader, the channel estimation filter operating to determine an estimate of an amplitude and phase associated with the pilot channel;

a conjugate generator coupled to the channel estimation filter, the conjugate generator operating to determine a complex conjugate of the estimate of the amplitude and phase associated with the pilot channel;

a traffic channel Walsh code despreader coupled to the first mixer, the traffic channel Walsh code despreader operating to despread the converted code division multiple access spread spectrum information signal;

a delay of channel estimation filter coupled to the traffic channel Walsh code despreader, the delay of channel estimation filter operating to determine an estimate of a delay necessary for proper time alignment of the pilot channel and the traffic channel for demodulation;

a second mixer coupled to the conjugate generator and to the delay of channel estimation filter, the second mixer operating to multiply the complex conjugate of the estimate of the phase and amplitude associated with the pilot channel by a delayed representation of the traffic channel;

a signal to noise ratio estimator coupled to at least one of the pilot channel Walsh code despreader and the traffic channel Walsh code despreader, the signal to noise ratio estimator operating to determine an estimated signal to noise ration associated with at least the traffic channel and generating a power control signal when the estimated signal to noise ratio associated with at least the traffic signal is other than a predetermined signal to noise ration necessary for optimal demodulation of information associated with the traffic channel;

a first magnitude squared generator coupled to the channel estimation filter, the magnitude squared generator operating to determine an estimated power associated with the pilot channel;

a third mixer coupled to the magnitude squared generator and an M-ary QAM constellation generator that operates to generate an M-ary QAM constellation vector reference, the third mixer operating to multiply the estimated power associated with the pilot channel by the M-ary QAM constellation vector reference;

a delay generator responsive to the power control signal and coupled to the third mixer, the delay generator operating to select a predetermined time delay after which a traffic channel gain is adjusted according to the power control signal;

a fourth mixer coupled to the third mixer and to the delay generator that provides an input signal representing the traffic channel gain, the fourth mixer operating to multiply a result of the third mixer by the traffic channel gain;

a fifth mixer coupled to the second mixer and having an input signal representing a pilot channel gain determined from a pilot channel power gain parameter broadcast to the fading resistant multi-level QAM receiver, the fifth mixer operating to multiply a result of the second mixer by the input signal representing the pilot channel gain;

a summer coupled to the fourth mixer and to the fifth mixer, the summer operating to subtract a result of the fourth mixer form a result of the fifth mixer;

a second magnitude squared generator coupled to the summer, the second magnitude squared generator operating to determine a Euclidean distance metric associated with each M-ary QAM modulation point;

a dual minima soft metric generator coupled to the second magnitude squared generator, the dual minima soft metric generator operating to generate a soft decision for each bit comprising a channel symbol;

a de-interleaver coupled to the dual minima soft metric generator, the de-interleaver operating to deinterleave the channel symbols; and a decoder coupled to the de-interleaver, the decoder operating to decode the channel symbols into information bits representing a transmitted message.

7. A fading resistant multi-level QAM receiver, comprising:

an antenna for receiving a code division multiple access spread spectrum information signal comprising a traffic channel and a pilot channel;

a first mixer coupled to the antenna, the first mixer operating to multiply the code division multiple access spread spectrum information signal by an appropriate pseudo-random numerical code sequence to generate a converted code division multiple access spread spectrum information signal;

a pilot channel Walsh code despreader coupled to the first mixer, the pilot channel Walsh code despreader operating to despread the converted code division multiple access spread spectrum information signal;

a channel estimation filter coupled to the pilot Walsh code despreader, the channel estimation filter operating to determine an estimate of an amplitude and phase associated with the pilot channel;

a conjugate generator coupled to the channel estimation filter, the conjugate generator operating to determine a complex conjugate of the estimate of the amplitude and phase associated with the pilot channel;

a traffic channel Walsh code despreader coupled to the first mixer, the traffic channel Walsh code despreader operating to despread the converted code division multiple access spread spectrum information signal;

a delay of channel estimation filter coupled to the traffic channel Walsh code despreader, the delay of channel estimation filter operating to determine an estimate of a delay necessary for proper time alignment of the pilot channel and the traffic channel for demodulation; and a second mixer coupled to the conjugate generator and to the delay of channel estimation filter, the second mixer operating to multiply the complex conjugate of the estimate of the phase and amplitude associated with the pilot channel by a delayed representation of the traffic channel.

8. The fading resistant multi-level QAM receiver of claim 7, comprising:

a magnitude generator coupled to the channel estimation filter, the magnitude generator operating to determine an estimated amplitude associated with the pilot channel;

an M-ary QAM constellation generator coupled to the magnitude generator, the M-ary QAM constellation generator operating to generate an M-ary QAM constellation vector reference;

a third mixer coupled to the magnitude generator and the M-ary QAM constellation generator, the third mixer operating to multiply the estimated power associated with the pilot channel by the M-ary QAM constellation vector reference;

a traffic channel gain estimator coupled to the traffic channel Walsh code despreader, the traffic channel gain estimator operating to determine an estimated amplitude associated with the traffic channel;

a fourth mixer coupled to the third mixer and to the traffic channel gain estimator, the fourth mixer operating to multiply a result of the third mixer by the estimated amplitude associated with the traffic channel; and a summer coupled to the second mixer and to the fourth mixer, the summer operating to subtract a result of the fourth mixer from a result of the second mixer.

9. The fading resistant multi-level QAM receiver of claim 8, further comprising:

a magnitude squared generator coupled to the summer, the magnitude squared generator operating to determine a Euclidean distance metric associated with each M-ary QAM modulation point;

a dual minima soft metric generator coupled to the magnitude squared generator, the dual minima soft metric generator operating to generate a soft decision for each bit comprising a channel symbol;

a de-interleaver coupled to the dual minima soft metric generator, the de-interleaver operating to deinterleave the channel symbols; and a decoder coupled to the de-interleaver, the decoder operating to decode the channel symbols into information bits representing a transmitted message.

10. The fading resistant multi-level QAM receiver of claim 7, comprising:

a first magnitude squared generator coupled to the channel estimation filter, the first magnitude squared generator operating to determine an estimated power associated with the pilot channel;

an M-ary QAM constellation generator that generates an M-ary QAM constellation vector reference;

a third mixer coupled to the first magnitude squared generator and the M-ary QAM constellation generator, the third mixer operating to multiply the magnitude of the estimated power associated with the pilot channel by the M-ary QAM constellation vector reference;

a fourth mixer coupled to the third mixer and having an input signal representing a traffic channel gain determined from a traffic channel power gain parameter broadcast to the fading resistant multi-level QAM receiver, the fourth mixer operating to multiply a result of the third mixer by the traffic channel gain;

a fifth mixer coupled to the second mixer and having an input signal representing a pilot channel gain determined form a pilot channel power gain parameter broadcast to the fading resistant multi-level QAM receiver, the fifth mixer operating to multiply a result of the second mixer by the input signal representing a pilot channel gain; and a summer coupled to the fourth mixer and to the seventh mixer, the summer operating to subtract a result of the fourth mixer form a result of the fifth mixer.

11. The fading resistant multi-level QAM receiver of claim 10, further comprising:

a second magnitude squared generator coupled to the summer, the second magnitude squared generator operating to determine a Euclidean distance metric associated with each M-ary QAM modulation point;

a dual minima soft metric generator coupled to the second magnitude squared generator, the dual minima soft metric generator operating to generate a soft decision for each bit comprising a channel symbol;

a de-interleaver coupled to the dual minima soft metric generator, the de-interleaver operating to deinterleave the channel symbols; and a decoder coupled to the de-interleaver, the decoder operating to decode the channel symbols into information bits representing a transmitted message.

12. The fading resistant multi-level QAM receiver of claim 7, comprising:

a signal to noise ratio estimator coupled to at least one of the pilot channel Walsh code despreader and the traffic channel Walsh code despreader, the signal to noise ratio estimator operating to determine an estimated signal to noise ratio associated with at least the traffic channel and generating a power control signal when the estimated signal to noise ratio associated with at least the traffic signal is other than a predetermined signal to noise ratio necessary for optimal demodulation of information associated with the traffic channel;

a first magnitude squared generator coupled to the channel estimation filter, the magnitude squared generator operating to determine an estimated power associated with the pilot channel;

an M-ary QAM constellation generator coupled to the first magnitude squared generator, the M-ary QAM constellation generator operating to generate an M-ary QAM constellation vector reference;

a third mixer coupled to the first magnitude squared generator and the M-ary QAM constellation generator, the third mixer operating to multiply the estimated power associated with the pilot channel by the M-ary QAM constellation vector reference;

a delay generator responsive to the power control signal and coupled to the third mixer, the delay generator operating to select a predetermined time delay after which a traffic channel gain is adjusted according to the power control signal;

a fourth mixer coupled to the third mixer and to the delay generator that provides an input signal representing the traffic channel gain, the fourth mixer operating to multiply a result of the third mixer by the traffic channel gain;

a fifth mixer coupled to the second mixer and having an input signal representing a pilot channel gain determined from a pilot channel power gain parameter broadcast to the fading resistant multi-level QAM receiver, the fifth mixer operating to multiply a result of the second mixer by the input signal representing the pilot channel gain; and a summer coupled to the fourth mixer and to the fifth mixer, the summer operating to subtract a result of the fourth mixer form a result of the fifth mixer.

13. The fading resistant multi-level QAM receiver of claim 12, further comprising:

a second magnitude squared generator coupled to the summer, the second magnitude squared generator operating to determine a Euclidean distance metric associated with each M-ary QAM modulation point;

a dual minima soft metric generator coupled to the second magnitude squared generator, the dual minima soft metric generator operating to generate a soft decision for each bit comprising a channel symbol;

a de-interleaver coupled to the dual minima soft metric generator, the de-interleaver operating to deinterleave the channel symbols; and a decoder coupled to the de-interleaver, the decoder operating to decode the channel symbols into information bits representing a transmitted message.

* * * * *